United States Patent
Chen

(10) Patent No.: US 10,363,310 B2
(45) Date of Patent: *Jul. 30, 2019

(54) PROTON INDUCED BORON CAPTURE THERAPY

(71) Applicant: James Chinan Chen, Rockville, MD (US)

(72) Inventor: James Chinan Chen, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/890,374

(22) Filed: Feb. 7, 2018

(65) Prior Publication Data

US 2018/0161431 A1    Jun. 14, 2018

Related U.S. Application Data

(62) Division of application No. 14/488,293, filed on Sep. 17, 2014.

(51) Int. Cl.
*A61K 41/00* (2006.01)
*A61N 5/10* (2006.01)

(52) U.S. Cl.
CPC ............ *A61K 41/0095* (2013.01); *A61N 5/10* (2013.01); *A61N 5/1028* (2013.01); *A61N 2005/109* (2013.01); *A61N 2005/1087* (2013.01); *A61N 2005/1098* (2013.01)

(58) Field of Classification Search
CPC ...................................................... A61K 41/00
See application file for complete search history.

(56) References Cited

FOREIGN PATENT DOCUMENTS

JP        2014177421 A    *    9/2014

OTHER PUBLICATIONS

Rolf F. Barth et al. Boron Neutron Capture Therapy of Brain Tumors: Enhanced Survival following Intracarotid Injection of either Sodium BOrocaptate ro Boronphenylalanine with or without Blood-Brain Barrier Disruption, Cancer Research 57, 1129-1136. (Year: 1997).*
Damien C. Weber et al. Spot-Scanning proton radiation therapy for recurrent, residual or untreated intracranial meningiomas, Radiotherapy and Oncology 71, 251-258. (Year: 2004).*
Rolf F. Brath et al., Boron Neutron Capture Therapy of Cancer: Current Status and Future Prosppects, Clin. Cancer Res; 11(11), 3987-4002. (Year: 2005).*
Daniel Miller, A review of proton beam radiation therapy, Med. Phys.22(11), 1943-1954. (Year: 1995).*

* cited by examiner

*Primary Examiner* — Michael G. Hartley
*Assistant Examiner* — Jagadishwar R Samala
(74) *Attorney, Agent, or Firm* — Chieh-Mei Wang

(57) ABSTRACT

The present disclosure provides methods of treating a biological tissue using a proton beam. A method includes the steps of: irradiating a proton beam to a biological tissue containing a reactant. The reactant includes a composite. The composite reacts with at least one proton from the proton beam and releases at least one $\alpha$ particle or $\gamma$ rays. The $\alpha$ particle or $\gamma$ rays reacts with the biological tissue. Another method includes the steps of: providing a reactant, the reactant comprising a composite; introducing the reactant into a biological tissue, the reactant being distributed in the biological tissue; and irradiating the biological tissue with the proton beam. The composite reacts with at least one proton from the proton beam to release at least one $\alpha$ particle or $\gamma$ rays, and the $\alpha$ particle or the $\gamma$ rays reacts with the biological tissue.

7 Claims, 5 Drawing Sheets

PROTON INDUCED BORON CAPTURE THERAPY

FIELD

The present disclosure relates to a method of treating biological tissues by radiation and, and more particularly, to a method of treating biological tissues with a proton beam.

BACKGROUND

An ever increasing number of people suffer from cancer. Surgery, radiation therapy and chemotherapy can treat some tumors. An alternative treatment of cancer therapy is Boron Neutron Captured Therapy (BNCT). During BNCT, a patient is injected with a boron compound highly enriched in $B^{10}$. The boronated compound concentrates preferentially in the cancer. The patient's tumor is then irradiated with thermal neutron beams which can be capture by boron in the tumor according to a $B^{10}$ $(n,\alpha)Li^7$ reaction. The distance of high linear energy transfer (LET) $\alpha$ particles in tissue is about the diameter of a cell. Therefore, a highly localized, specific reaction takes place whereby the tumor receives a larger radiation dose, compared to that received by the surrounding healthy tissue, from the transit of the thermal neutrons.

The rapid attenuation of the thermal neutron flux and random scattering are the major problems of BNCT. These prevent effective treatment of the deep tumors. A large proportion of neutrons seldom reaches the tumor, but damages the normal cells instead.

BRIEF DESCRIPTION OF THE DRAWINGS

The present disclosure will become more fully understood from the detailed description of preferred embodiments given herein below with reference to the drawings.

DETAILED DESCRIPTION

The present disclosure will be apparent from the following detailed description, which proceeds with reference to the accompanying drawings, wherein the same references relate to the same elements.

To improve BNCT, the present disclosure provides a method of treating tumor tissues with proton induced boron capture therapy (PiBCT).

The proposed proton induced boron capture therapy comprises: irradiating a proton beam to a biological tissue containing a reactant, and wherein said reactant comprising a first composite and a second composite; said first composite to react with at least one proton from said proton beam and then release at least one neutron inside said biological tissue; said second composite to react with said at least one said neutron to release at least one $\alpha$ particle or $\gamma$ rays, and said $\alpha$ particle or said $\gamma$ rays to react with said biological tissue.

In an embodiment, the second composite containing $^{10}B$ and is selected from the group consisting of BPA, BSH, carbohydrate derivatives of (L)-4-dihydroxy-borylphenylalanine (BPA), sodium mercaptoun decahydro-closo-dodecaborate (BSH), carbohydrate derivatives of BSH, sodium salt of closo-$B_{10}H_{10}^{2-}$ (GB-10), β-5-o-carboranyl-2V-deoxyuridine (D-CDU), 3-(dihydroxypropyl-carboranyl-pentyl) thymidine derivative (N5-2OH), boron-containing porphyrins ($H_2DCP$), dequalinium derivatives (DEQ-B), derivatives of trimethoxyindoles, aziridines, derivatives of acridines, phenanthridines, carboranyl polyamines, Pt(II)-amine complexes, dibenzimidazoles, tribenzimidazoles, glucose molecules, mannose molecules, ribose molecules, gulose molecules, fucose molecules, galactose molecules, maltose molecules, lactose molecules, phosphates, phosphonates, phenylureas, thioureas, nitroimidazoles, amines, benzamides, isocyanates, nicotinamides, or azulenes.

In an embodiment, the first composite is selected from the group consisting of $^7Li$ and $^9Be$ In an embodiment, the proton beam irradiates the biological tissue in a spot scanning manner, uniform scanning manner, fast scanning manner, or scatter manner.

In an embodiment, the proton beam obtains appropriate energy and transmits to the biological tissue by cyclotron or synchrotron.

In an embodiment, the reactant is introduced into said biological tissue through a catheter.

In an embodiment, the reactant is introduced into said biological tissue through intramuscular manner, intravenous manner, oral manner, or subcutaneous manner.

In an embodiment, the intravenous manner includes intravenous infusion admixture, intravenous drip, or intravenous push.

In PiBCT of the present disclosure, neutrons react with tumor directly. Thus, neutron energy will not decrease and normal tissue will not be damaged.

In PiBCT of the present disclosure, the biocompatibility of said reactant is confirmed in irradiation therapy. Unexceptional effects to human will not occur.

Figure 1:
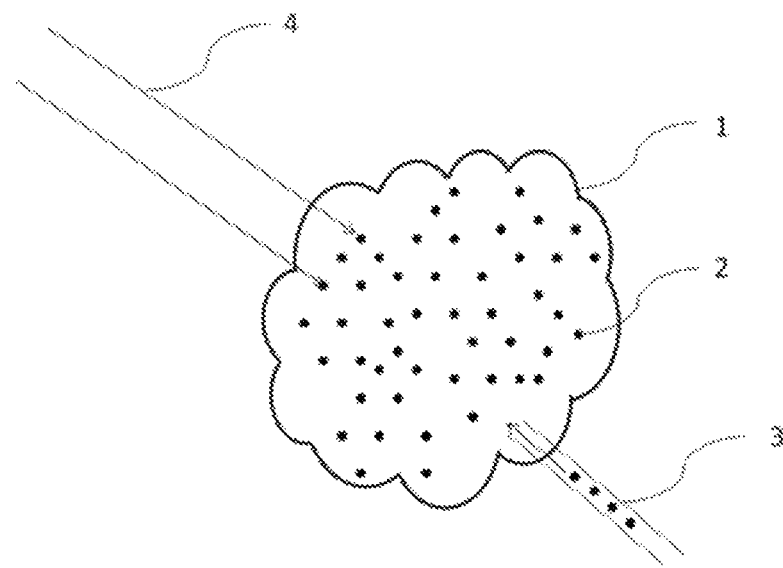
FIG. 1 diagrammatically illustrates treatment of biological tissue with PiBCT in accordance with one embodiment of the present disclosure.

The following paragraphs describe embodiments of the disclosed method of treating biological tissue with a proton beam. As shown in FIG. 1, a reactant 2 is introduced to the target biological tissue 1 by a clinical catheter 3, so the reactant 2 is distributed in the target biological tissue 1. A proton beam 4 irradiates the target biological tissue 1, and the reactant 2 absorbs protons and releases neutrons. The neutrons are released from reactant 2 distributed in the target biological tissue 1 and further reacts with reactant 2 to release $\alpha$ particles or $\gamma$ rays. These $\alpha$ particles or $\gamma$ rays damage the cells of the target biological tissues 1.

The reactant 2 is a mixture or compound that contains a first composite and a second composite. The reactant 2 reacts with protons and neutrons successively to produce $\alpha$ particles or $\gamma$ rays. Specifically, the first composite absorbs protons and releases neutrons while the second composite absorbs neutrons and release $\alpha$ particles or $\gamma$ rays. Preferably, the second composite is one of the boron-10 ($^{10}B$) containing reactants including but not being limited to BPA, BSH, carbohydrate derivatives of BSH, GB-10, D-CDU, N5-2OH, H2DCP, DEQ-B, derivatives of trimethoxyindoles, aziridines, derivatives of acridines, phenanthridines, carboranyl polyamines, Pt(II)-amine complexes, dibenzimidazoles, tribenzimidazoles, glucose molecules, mannose molecules, ribose molecules, gulose molecules, fucose molecules, galactose molecules, maltose molecules, lactose molecules, phosphates, phosphonates, phenylureas, thioureas, nitroimidazoles, amines, benzamides, isocyanates, nicotinamides, or azulenes. $^{10}B$ tends to absorb thermal neutrons having energy less than 0.5 electron volts and will temporarily becomes $^{11}B$, which decays instantly to release an α particle or γ-rays. The first composite is selected according to the selection of the second composite and should be a composite to absorb protons and release neutrons. The first composite can be selected from the group consisting of $^7Li$ or $^9Be$ when taking bombarding energy, neutron production rate, target melting point, and target thermal conductivity into consideration. Preferably, $^7Li$ is better for the first composite of the invention due to the convenient access for it and the poisonous character of $^9Be$.

Figure 2:
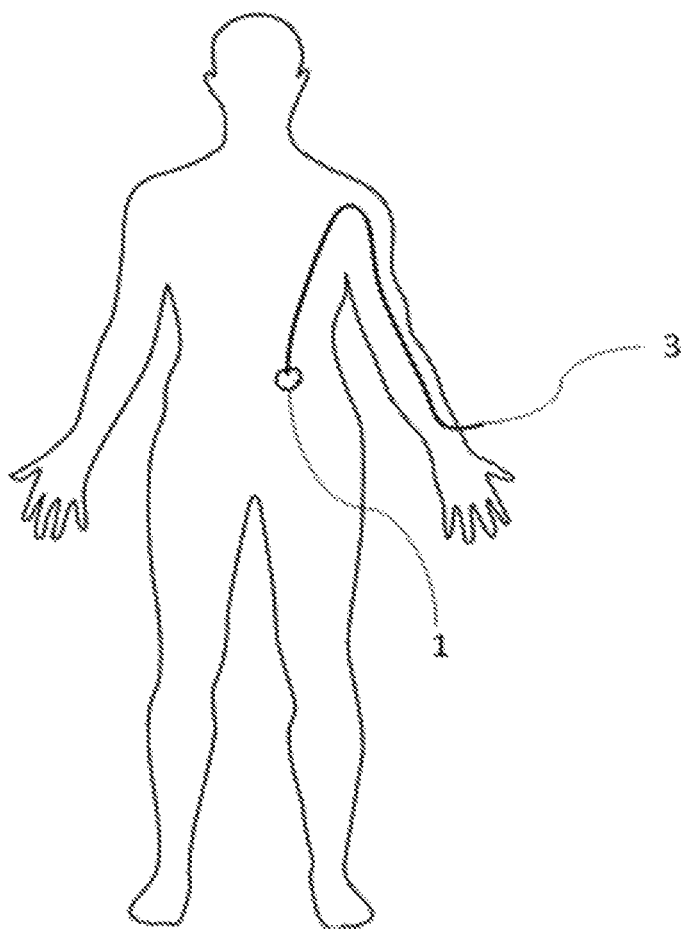
FIG. 2 diagrammatically illustrates treatment of a biological tissue with PiBCT wherein a catheter is used to introduce reactant into a biological tissue inside a human body in accordance with one embodiment of the present disclosure.

In addition, as shown in FIG. 2, a clinical catheter 3 is used to introduce the reactant 2 to the target biological tissue 1 into a human body. The clinical catheter 3 can be embedded into the human body through intramuscular manner, intravenous manner, oral manner, or subcutaneous manner and then be extended to the target biological tissue 1 along the vein. The intravenous manner includes intravenous infusion admixture, intravenous drip, or intravenous push. An Intravenous infusion admixture is to use a syringe or other device to extract the reactant from the sterile container, and impose directly into patient's vein. An Intravenous drip uses gravity or automated device to control the rate of delivering reactant into patient's vein. An Intravenous push involves pushing reactant into patient's vein manually or mechanically through syringe or other device.

As a result, the reactant 2 will distribute in the target biological tissue 1 and the reactant 2 in the target biological tissue 1 can react with neutrons when the target biological tissue 1 is irradiated by a proton beam 4.

Figure 3:
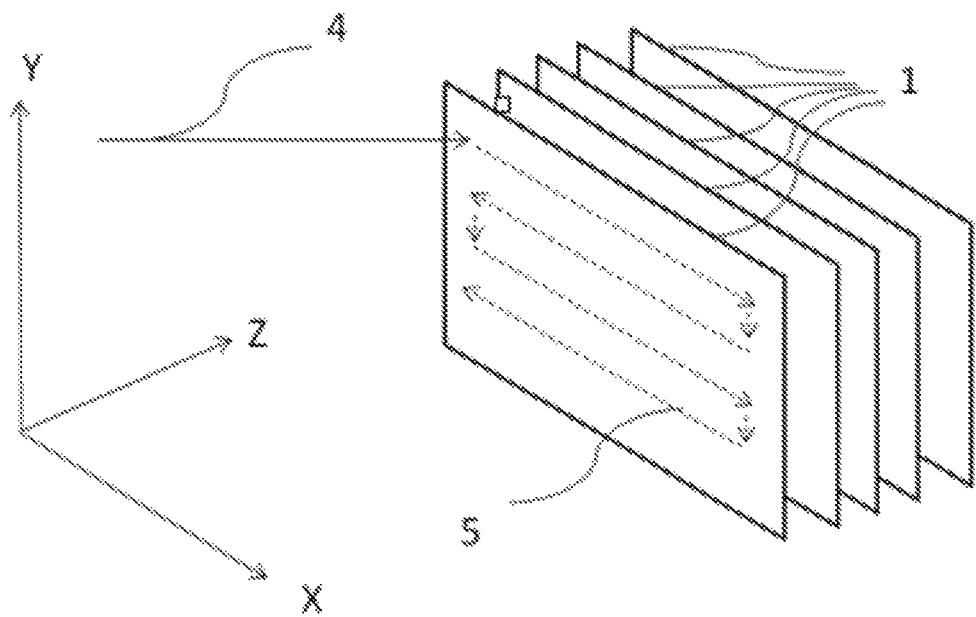
FIG. 3 diagrammatically illustrates treatment of a biological tissue with PiBCT wherein a spot scanning process of a proton beam is performed in accordance with one embodiment of the present disclosure.

As shown in FIG. 3, the target biological tissues 1 are uniformly irradiated with photon beams in a spot scanning manner in accordance with an embodiment of the invention. The target biological tissues 1 can be regarded as being composed of a plurality of layers in the X-Y plane with each of the layers being parallel with each other. The proton beam 4 brings an adjustable specific intensity to be irradiated to each layer of the target biological tissues 1. The proton beam 4 moves along a long path in parallel to the X-axis and then a short path in parallel to the Y-axis and repeats this procedure to complete the irradiating path 5 shown in FIG. 3. After the proton beam 4 completes an irradiation for one layer of the target biological tissues 1, the intensity of the proton beam 4 is adjusted for irradiation of another layer of the target biological tissues 1. The above mentioned procedures are continually performed to complete all layers of the target biological tissues 1. The scanning method is not limited to spot scanning, but can also be uniform scanning, fast scanning, or scatter. In one embodiment, the proton beam 4 obtains appropriate energy by cyclotron or synchrotron.

Figure 4:
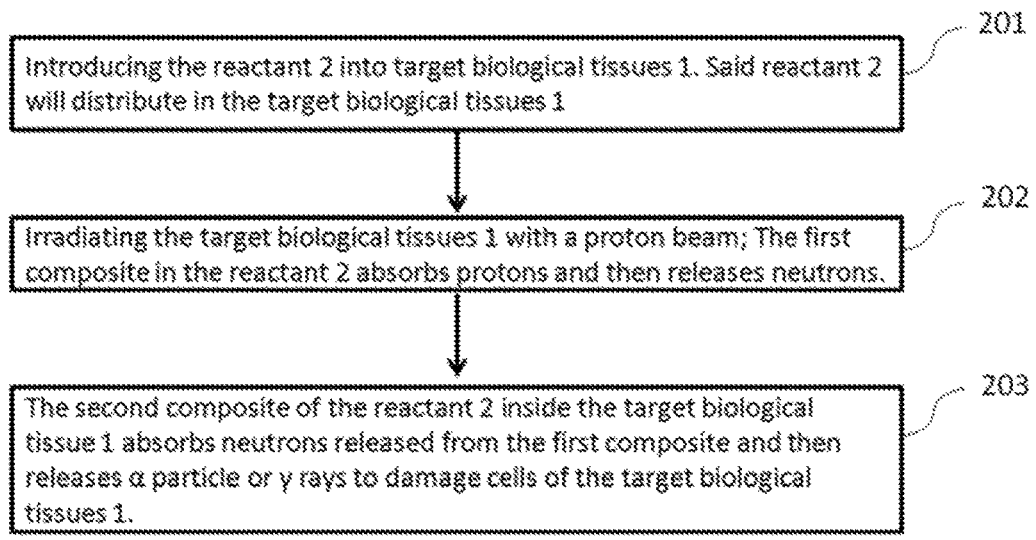
FIG. 4 is a flow chart illustrating a method of treating biological tissues with PiBCT in accordance with one embodiment of the present disclosure.

FIG. 4 is a flow chart illustrating a method of providing reactant 2 and treating biological tissues with PiBCT. The reactant 2 contains a first composite and a second composite; Said first composite can be selected from the group consisting of $^7Li$ or $^9Be$; Said second composite is one of the boron-10 ($^{10}B$) containing reactants including but not being limited to BPA, BSH, carbohydrate derivatives of BSH, GB-10, D-CDU, N5-2OH, H2DCP, DEQ-B, derivatives of trimethoxyindoles, aziridines, derivatives of acridines, phenanthridines, carboranyl polyamines, Pt(II)-amine complexes, dibenzimidazoles, tribenzimidazoles, glucose molecules, mannose molecules, ribose molecules, gulose molecules, fucose molecules, galactose molecules, maltose molecules, lactose molecules, phosphates, phosphonates, phenylureas, thioureas, nitroimidazoles, amines, benzamides, isocyanates, nicotinamides, or azulenes.is The method includes the following steps.

In block 201, the reactant 2 is introduced into target biological tissues 1. The reactant 2 will distribute in the target biological tissues 1 as FIG. 1 shown. In an embodiment, the reactant 2 is introduced into the target biological tissues 1 by a clinical catheter 3. As shown in FIG. 2, the clinical catheter 3 can be embedded into a human body with an intravenous therapy and be extended to the target biological tissue 1 along the vein, so that the reactant 2 is able to be introduced to the target biological tissue 1.

In block 202, the target biological tissues 1 are irradiated with a proton beam 4 as shown in FIG. 1. The first composite in the reactant 2 absorbs protons and then releases neutrons. In an embodiment, the proton beam 4 obtains appropriate energy and transmits to the target biological tissues by cyclotron or synchrotron. In an embodiment, as shown in FIG. 2, the proton beam 4 is irradiated to the tamet biological tissues 1 in a spot scanning manner.

In block 203, the second composite of the reactant 2 inside the target biological tissue 1 absorbs neutrons released from the first composite and then releases α particle or γ rays to damage cells of the target biological tissues 1.

Figure 5:
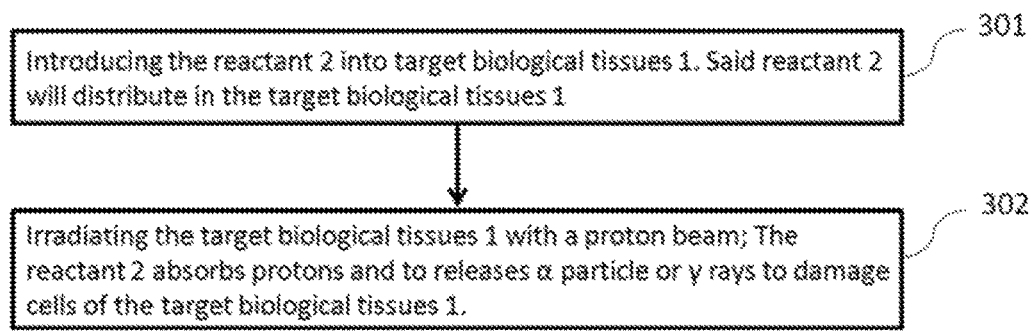
FIG. 5 is a flow chart illustrating a method of treating biological tissues with PiBCT in accordance with another embodiment of the present disclosure.

FIG. 5 is a flow chart illustrating another method of providing reactant 2 and treating biological tissues with PiBCT. The reactant 2 contains a composite; Said composite is one of the boron-10 ($^{10}B$) containing reactants including but not being limited to BPA, BSH, carbohydrate derivatives of BSH, GB-10, D-CDU, N5-2OH, H2DCP, DEQ-B, derivatives of trimethoxyindoles, aziridines, derivatives of acridines, phenanthridines, carboranyl polyamines, Pt(II)-amine complexes, dibenzimidazoles, tribenzimidazoles, glucose molecules, mannose molecules, ribose molecules, gulose molecules, fucose molecules, galactose molecules, maltose molecules, lactose molecules, phosphates, phosphonates, phenylureas, thioureas, nitroimidazoles, amines, benzamides, isocyanates, nicotinamides, or azulenes. The method includes the following steps.

In block 301, the reactant 2 is introduced into target biological tissues 1. Said reactant 2 will distribute in the target biological tissues 1 as FIG. 1 shown. In an embodiment, the reactant 2 is introduced into the target biological tissues 1 by a clinical catheter 3. As shown in FIG. 2, the clinical catheter 3 can be embedded into a human body with an intravenous therapy and be extended to the target biological tissue 1 along the vein, so that the reactant 2 is able to be introduced to the target biological tissue 1.

In block 302, the target biological tissues 1 are irradiated with a proton beam 4 as shown in FIG1. The composite of the reactant 2 inside the target biological tissue 1 absorbs protons and then releases α particle or γ rays to damage cells of the target biological tissues 1. In an embodiment, the proton beam 4 obtains appropriate energy and transmits to the target biological tissues by cyclotron or synchrotron. In an embodiment, as shown in FIG. 2, the proton beam 4 is irradiated to the target biological tissues 1 in a spot scanning manner.

The target biological tissues 1 are but not limited to tumors in a patient's body.

In comparison with BNCT, the PiBCT of the invention utilizes irradiation of a proton beam to release neutrons inside the target biological tissue 1 and therefore to avoid energy dissipation of the neutrons outside the target biological tissue 1. Also, the neutrons released from the first composite interact with the second composite in the target biological tissues 1 and do not affect the other normal tissues beside the target biological tissues 1. Moreover, the PiBCT is performed to spot scan the target biological tissue 1 with the proton beam 4 in a regular direction and provides fewer doses to normal tissues beside the target biological tissue 1 than the random scattering neutron beam in BNCT does.

In an embodiment of the invention, the reactant 2 contains boronated compound that have been widely used, such as $^7$Li.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A method of treating a biological tissue using a proton beam, comprising steps of:
   introducing a reactant into a biological tissue, the reactant comprising a composite and being distributed in the biological tissue; and
   irradiating the biological tissue with the proton beam,
   wherein the composite comprises $^{10}$B and $^{11}$B, the composite reacts with at least one proton from the proton beam to release at least one α particle or γ rays, and the α particle or the γ rays reacts with the biological tissue.

2. The method of treating a biological tissue using a proton beam according to claim 1, wherein the composite is, selected from a group consisting of (L)-4-dihydroxy-borylphenylalanine (BPA), sodium mercaptoun decahydro-closo-dodecaborate (BSH), carbohydrate derivatives of BSH, sodium salt of closo-$B_{10}H_{10}^{2-}$ (GB-10), β-5-o-carboranyl-2V-deoxyuridine (D-CDU), 3-(dihydroxypropyl-carboranyl-pentyl) thymidine derivative (N5-20H), boron-containing porphyrins ($H_2$DCP), dequalinium derivatives (DEQ-B), derivatives of trimethoxyindoles, aziridines, derivatives of acridines, phenanthridines, carboranyl polyamines, Pt(II)-amine complexes, dibenzimidazoles, tribenzimidazoles, glucose molecules mannose molecules, ribose molecules, gulose molecules, fucose molecules, galactose molecules, maltose molecules, lactose molecules, phosphates, phosphonates, phenylureas, thioureas, nitroimidazoles, amines, benzamides, isocyanates, nicotinamides, or azulenes.

3. The method of treating, a biological tissue using a proton beam according to claim 1, wherein the proton beam irradiates the biological tissue in a spot scanning manner, uniform scanning manner, fast scanning manner, or scatter manner.

4. The method of treating a biological tissue using a proton beam according to claim 1, wherein the proton beam obtains appropriate energy and transmits to the biological tissue by cyclotron or synchrotron.

5. The method of treating a biological tissue using a proton beam according to claim 1, wherein the reactant is introduced into the biological tissue by a catheter or a drug carrier.

6. The method of treating biological tissues using a proton beam according to claim 1, wherein the reactant is introduced into the biological tissue in an intramuscular manner, intravenous manner, oral manner, or subcutaneous manner.

7. The method of treating biological tissues using a proton beam according to claim 6, wherein the intravenous manner comprises an intravenous infusion admixture, an intravenous drip, or an intravenous push.

* * * * *